United States Patent [19]
Schrepfer et al.

[11] 4,198,354
[45] Apr. 15, 1980

[54] MANUFACTURE OF α-FORMYLETHANEPHOSPHONIC ACID ESTERS

[75] Inventors: Hans J. Schrepfer, Ludwigshafen; Hardo Siegel, Speyer; Hans Theobald, Limburgerhof, all of Fed. Rep. of Germany

[73] Assignee: BASF Aktiengesellschaft, Fed. Rep. of Germany

[21] Appl. No.: 888,510

[22] Filed: Mar. 20, 1978

[30] Foreign Application Priority Data
Apr. 9, 1977 [DE] Fed. Rep. of Germany ....... 2715923

[51] Int. Cl.$^2$ .............................................. C07F 9/40
[52] U.S. Cl. .................................................... 260/968
[58] Field of Search ................................ 260/968, 946

[56] References Cited
PUBLICATIONS

Moskva et al., "J. Gen. Chem. USSR" (English Translation) vol. 41, pp. 1687–1691, (1971).
Reichel et al., "Ann. Chem.," vol. 751 (1971), p. 69.
Moskva et al., "J. G. Chem. USSR" (English Translation) vol. 41, (1971) pp. 1489–1492.
Wagner et al., "Synthetic Organic Chemistry", (1953), p. 282.

*Primary Examiner*—Anton H. Sutto
*Attorney, Agent, or Firm*—Keil & Witherspoon

[57] ABSTRACT

α-Formylethane-phosphonic acid esters are manufactured by reacting vinylphosphonic acid esters with carbon monoxide and hydrogen in the presence of conventional rhodium-containing hydroformylation catalysts. The reaction is carried out at from 50° to 180° C. and at pressures from 20 to 1,500 bars. The products are intermediates for the synthesis of insecticidally active phosphoric acid ester derivatives.

2 Claims, No Drawings

MANUFACTURE OF α-FORMYLETHANEPHOSPHONIC ACID ESTERS

The present invention relates to the manufacture of α-formyl-ethanephosphonic acid esters by hydroformylation of vinylphosphonic acid esters.

Ann. Chem. 751 (1971), 69–76 and J. Gen. Chem. USSR 41 (1971), 1,687–1,691 disclose that α-formylphosphonic acid esters are obtained by acid hydrolysis of 2-alkoxy-1-alkyl-vinyl-phosphonic acid esters. A disadvantage of this method of synthesis is that the starting materials are very difficult to obtain. 2-Alkoxy-1-alkylvinyl-phosphonic acid esters can only be prepared via several reaction stages, either by the action of a trialkyl phosphite on α-bromoaldehyde-acetals, the yield being only 10% (Ann. Chem. 751 (1971), 74) or by the action of a threefold molar amount of phosphorus pentachloride on acetals, where the complex salts first produced must be decomposed with sulfur dioxide, and subsequent esterification with sodium alcoholates (J. Gen. Chem. USSR 41 (1971), 1,494–1,996).

We have found that α-formylethane-phosphonic acid esters of the formula I

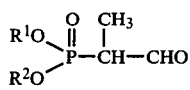

where $R^1$ and $R^2$ are identical or different and are unbranched or branched alkyl of 1 to 5 carbon atoms, are obtained by reacting vinylphosphonic acid esters of the formula II

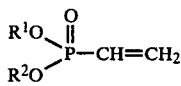

where $R^1$ $R^2$ have the above meanings, with carbon monoxide and hydrogen in the presence of conventional rhodium-containing hydroformylation catalysts at from 50° to 180° C. and under a pressure of from 20 to 1,500 bars.

Using the process according to the invention, α-formylethane-phosphonic acid esters (which are valuable intermediates for the manufacture of the insecticidally active phosphoric acid esters of the formula:

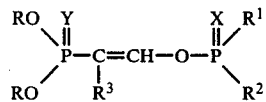

where R denotes linear or branched alkyl of a maximum of 6 carbon atoms, $R^1$ denotes linear or branched alkyl or alkoxy of a maximum of 6 carbon atoms, linear or branched alkynyloxy of a maximum of 4 carbon atoms, phenyl, phenyl mono- or polysubstituted by halogen or alkyl of 1 to 4 carbon atoms, or benzyloxy, $R^2$ denotes alkoxy, alkylthio, alkylamino or dialkylamino, (alkyl in these radicals being linear or branched and of a maximum of 6 carbon atoms), linear or branched alkynyloxy of a maximum of 4 carbon atoms, or benzyloxy, $R^3$ denotes hydrogen or linear or branched alkyl of a maximum of 3 carbon atoms, X denotes oxygen or sulfur, and Y denotes oxygen or sulfur, which form the subject matter of Patent Application U.S. Pat. No. 2,715,924 (U.S. application Ser. No. 889,834) are obtained in a simple manner from readily obtainable starting materials.

The products of the formula I are α-formylethane-phosphonic acid dialkyl esters, where alkyl is of 1 to 5 carbon atoms and is unbranched or branched. For example, $R^1$ and $R^2$ in formula I are methyl, ethyl, n-propyl, i-propyl, butyl or pentyl. Esters where $R^1$ and $R^2$ are identical and are methyl, ethyl or isopropyl are preferred.

Some of the above compounds have previously been disclosed; however, the dimethyl, diisopropyl and di-n-butyl esters of α-formylethane-phosphonic acid, as well as esters of the formula I, where $R^1$ and $R^2$ are different and are each unbranched or branched alkyl of 1 to 5 carbon atoms, are new.

The vinylphosphonic acid esters of the formula II used as starting materials have been disclosed and can be obtained, for example, by reacting vinylphosphonic acid dichloride with alcohols in the presence of bases or by reacting trialkyl phosphites with vinyl chloride in an autoclave at 190° C. in the presence of nickel-II chloride as the catalyst (Kosolapoff and Maier, Organic Phosphorus Compounds, volume 7, page 108 (1976); Tetrahedron 26 (1970), 5,529–5,534).

The hydroformylation of the compounds of the formula II is carried out in the conventional manner. Suitable catalysts are conventional rhodium-containing hydroformylation catalysts. Examples of these are finely divided metallic rhodium, rhodium carbonyls, rhodium chloride, rhodium nitrate, rhodium sulfate, rhodium oxides, fatty acid salts of rhodium and complex compounds which are obtained by reacting rhodium salts or rhodium carbonyl compounds with triphenylphosphine, olefins, diolefins or acetylacetone. Square planar rhodium-(I) complexes which are homogeneously soluble in the reaction mixture, e.g. dimeric rhodium carbonyl chloride, dimeric cycloocta-1,5-dienyl-rhodium chloride or rhodium carbonyl acetylacetonate, are preferred.

Catalysts of the type of $(PR_3)_n RhX(CO)$ or $(PR_3)_n HRh(CO)$, where $PR_3$ is preferably a triarylphosphine, especially triphenylphosphine, n is from 0.25 to 30 and X is chloride, bromide or iodide may also be employed; examples include tris-(triphenylphosphine)-rhodium carbonyl chloride and hydro-carbonyl-tris-(triphenylphosphine)-rhodium-(I).

The hydroformylation can be carried out with previously synthesized rhodium carbonyl complexes; equally, the complex can be formed in situ, under the reaction conditions, for example from rhodium halides, rhodium oxides, rhodium chelates or fatty acid salts of rhodium.

The amount of rhodium employed in the form of the hydroformylation catalyst is as a rule from 0.001 to 5,000 ppm, based on vinylphosphonic acid ester of the formula II. Amounts of from 0.5 to 500 ppm have proved particularly suitable.

Carbon monoxide and hydrogen are in general employed in a volume ratio of from 1:4 to 4:1, especially from 1:2 to 2:1. Advantageously, the gaseous mixture of carbon monoxide and hydrogen is employed in at least the stoichiometric amount, advantageously in excess, for example in up to 100 times the molar amount, based on the starting materials employed of the formula II.

The reaction is in general carried out at from 50° to 180° C. Temperatures of from 60° to 130° C. have proved particularly suitable. The pressure is as a rule from 20 to 1,500 bars and particularly advantageously from 100 to 700 bars.

The hydroformylation can be carried out continuously or batchwise.

Advantageously, the hydroformylation is carried out in the presence of an inert organic solvent. Examples of suitable solvents are aliphatic hydrocarbons, e.g. pentane, hexane and petroleum ether; cycloaliphatic hydrocarbons, e.g. cyclohexane, methylcyclohexane and cyclooctane; aromatic hydrocarbons, e.g. benzene, toluene and xylenes; aliphatic alkanols, e.g. methanol, ethanol and butanols; ethers, e.g. tetrahydrofuran and 1,3-dioxane, and mixtures of these solvents. Toluene and hexane are particularly suitable solvents. In general, the solvent is used in such amount as to give solutions of the starting material of from 10 to 80 percent strength by weight.

The reaction can also be carried out without added solvent. In that case, the compounds used as the starting material, and their hydroformylation products, serve as the solvent.

Advantageously, the α-formylethane-phosphonic acid esters are prepared by introducing the starting compound of the formula II, together with the catalyst, into a high pressure reaction vessel and carrying out the reaction with carbon monoxide and hydrogen, in the presence or absence of a solvent, under the above conditions. Given a suitable apparatus, the reaction can also, without difficulty, be carried out continuously. After cooling and letting down, the hydroformylation products are isolated by fractional distillation.

The Examples which follow illustrate the preparation of the compounds of the formula I.

EXAMPLE 1

In an autoclave of 1 liter capacity, fitted with a magnetic lift-stirrer, 113 g of vinylphosphonic acid dimethyl ester and 100 ppm of rhodium in the form of dimeric cycloocta-1,5-dienyl-rhodium chloride, in 600 ml of toluene as the solvent, are heated at 80° C. and reacted, under a pressure of 600 bars, with a mixture of carbon monoxide and hydrogen in the ratio of 1:1. The pressure is maintained for 12 hours by admitting further gas mixture. The reaction mixture is then allowed to cool under pressure, after which the autoclave is let down. The reaction mixture is worked up by distillation. 91 g of α-formylethane-phosphonic acid dimethyl ester, of boiling point 86°–90° C./0.1 mm Hg, are obtained.

EXAMPLE 2

Using the method described in Example 1, 228 g of vinylphosphonic acid diethyl ester give 191 g of α-formylethane-phosphonic acid diethyl ester, of boiling point 113° C./11 mm Hg.

EXAMPLE 3

Using the method described in Example 1, 89 g of vinylphosphonic acid diisopropyl ester give 28 g of α-formylethanephosphonic acid diisopropyl ester, of boiling point 130° C./20 mm Hg.

We claim:

1. A process for the manufacture of an α-formylethanephosphonic acid ester of the formula I

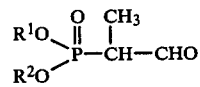

where $R^1$ and $R^2$ are identical or different and are unbranched or branched alkyl or 1 to 5 carbon atoms, wherein a vinylphosphonic acid ester of the formula II

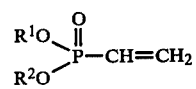

where $R^1$ and $R^2$ have the above meanings, is reacted with carbon monoxide and hydrogen in the presence of a rhodium-containing hydroformylation catalyst at from 50° to 180° C. and under a pressure of from 20 to 1,500 bars.

2. A process as claimed in claim 1, wherein the reaction is carried out in the presence of an inert organic solvent.

* * * * *